United States Patent [19]

Theeuwes et al.

[11] Patent Number: 4,904,474
[45] Date of Patent: Feb. 27, 1990

[54] DELIVERY OF DRUG TO COLON BY ORAL DOSAGE FORM

[75] Inventors: Felix Theeuwes, Los Altos; George V. Guittard, Cupertino; Patrick S. L. Wong, Hayward, all of Calif.

[73] Assignee: Alza Corporation, Palo Alto, Calif.

[21] Appl. No.: 147,840

[22] Filed: Jan. 25, 1988

[51] Int. Cl.⁴ .................. A61M 31/00; A61M 7/00
[52] U.S. Cl. .................. 424/424; 424/426; 424/468
[58] Field of Search ............. 424/468, 457, 424, 425, 424/426, 438

[56] References Cited

U.S. PATENT DOCUMENTS

| | | | |
|---|---|---|---|
| 4,278,087 | 7/1981 | Theeuves | 424/424 X |
| 4,309,996 | 1/1982 | Theeuwes | 424/424 X |
| 4,320,759 | 3/1982 | Theeuwes | 424/424 |
| 4,326,525 | 4/1982 | Swanson et al. | 424/424 X |
| 4,449,983 | 5/1984 | Cortese et al. | 424/424 X |
| 4,578,075 | 3/1986 | Urquhart et al. | 604/892 |
| 4,587,117 | 5/1986 | Edgren et al. | 424/15 |
| 4,627,851 | 12/1986 | Wong et al. | 604/892 |
| 4,642,232 | 2/1987 | Yman | 424/457 X |
| 4,693,895 | 9/1987 | Wong et al. | 424/473 |
| 4,705,515 | 11/1987 | Wong et al. | 604/892 |
| 4,748,023 | 5/1988 | Tamás et al. | 424/468 X |

Primary Examiner—Nancy A. B. Swisher
Attorney, Agent, or Firm—Paul L. Sabatine; Edward L. Mandell; Steven F. Stone

[57] ABSTRACT

A drug delivery device is disclosed for delivering a drug to the colon. The device comprises means for delaying the delivery of drug in the stomach, means for delaying delivery of drug in the small intestine, and means for delivering drug in the colon.

22 Claims, 5 Drawing Sheets

DELIVERY OF DRUG TO COLON BY ORAL DOSAGE FORM

FIELD OF THE INVENTION

The present invention pertains to the delivery of a beneficial drug to a preselected region of the gastrointestinal tract, specifically the colon. More particularly, the invention relates to both a novel and useful dosage form and to a method for delivering a beneficial drug to the colon.

BACKGROUND OF THE INVENTION

The delivery of a beneficial drug in the colon is therapeutically indicated for the treatment of inflammatory bowel disease, colitis ulcerosa, enteritis regionalis Crohn, chronic nonspecific colitis and diverticulitis. A critical and a pressing need exists for a dosage form for orally administering a beneficial drug for the management of these diseases and ailments of the colon. An oral dosage form is needed and it would be of a particular value in the management of disease and ailments of the colon that require colon-targeted delivery of a beneficial drug. Specifically, the dosage form would have a therapeutic value where therapy indicates the need for local, topical colon delivery of a beneficial drug to an affected colon site.

Prior to this invention tablets, capsules, and the like, were orally administered for delivering a beneficial drug to the colon. However, these prior art dosage forms delivered the drug throughout the entire length of the gastrointestinal tract. Moreover, the prior art dosage forms suffered with some disadvantages. For example, for some drugs a considerable amount of the drug dispensed by tablets and capsules is inactivated by the stomach because of the acidic and enzymatic environment of the stomach. Consequently the drug never reaches the colon to produce its intended effect. Additionally, most drug are metabolized or absorbed in the small intestine from such immediate release or sustained release forms. Thus, very little of the drug is available for producing a therapeutic result in the colon. The delivery of a drug through the rectum using suppositories, or by an enema, often leads to colon therapy, but rectal administration is inconvenient and messy and it is not readily accepted by the patient population. Also, drug delivery from suppositories cannot reach most of the colon as suppositories are self-limiting to the immediate area of administration.

In view of the above presentation it is immediately self-evident that a need exists for an oral dosage form that delays the onset of delivery for a period of time for the dosage form to reach the colon. Such a period of time corresponds to the time required for the dosage form to transit through the stomach and the small intestine and then commence delivery of a drug about the time the dosage form arrives at the colon.

OBJECTS OF THE INVENTION

It is an immediate object of this invention to provide a novel dosage form for dispensing a beneficial drug to produce a therapeutic effect, which dosage form overcomes the aforesaid disadvantages associated with the prior art dosage forms.

It is another object of this invention to provide a dosage form manufactured as an osmotic device for delivering a drug to a preselected area of the gastrointestinal tract of a warm blooded animal.

It is another object of this invention to provide an osmotic device for the controlled delivery of a beneficial drug to the colon, which delivery device represents an advance in colon-specific therapy.

It is another object of this invention to provide an osmotic delivery device for dispensing a drug to the colon of the gastro-intestinal tract of an animal for topical therapy.

It is another object of this invention to provide an osmotic delivery device for dispensing a drug to the colon of the gastro-intestinal tract of an animal for systemic therapy.

It is another object of this invention to provide an osmotic dosage device that delays the onset of drug release from the osmotic device for a period of time required for the osmotic device to pass through the stomach and the small intestine.

It is another object of this invention to provide a delayed-release osmotic device for topical-colonic therapy by the oral route.

It is another object of this invention to provide an osmotic device comprising a semipermeable wall that surrounds a compartment which compartment comprises means for delaying the delivery of drug from the osmotic device during the period of time required for the osmotic device to pass through the small intestine of a human.

It is another object of this invention to provide an osmotic device comprising a semipermeable wall carrying on its outer surface means for delaying the delivery of a drug from the osmotic device during the time required for the osmotic device to pass through the stomach.

It is another object of this invention to provide an osmotic device comprising a semipermeable wall that surrounds a compartment and which device comprises in combination means for delaying the delivery of drug during the time required for the osmotic device to travel through the stomach, and means for delaying the delivery of drug during the time required for the osmotic device to travel through the small intestine.

It is another object of this invention to provide an osmotic device comprising a wall that surrounds a compartment, a first means that surround the exterior surface of the wall for delaying delivery of a drug in the stomach, a second means in the compartment for delaying delivery of a drug in the intestine, and which first and second means operate in succession for delivering a drug in the colon.

Other objects, features, aspects and advantages of this invention will be more apparent to those versed in the dispensing art from the following detailed specification taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows:

FIG. 2 is an opened view of the osmotic device of FIG. 1, wherein FIG. 2 depicts the osmotic device shaped and adapted for passage through the stomach and small intestine substantially free of drug delivery in said stomach and small intestine;

FIG. 3 is an opened view of the osmotic device of FIG. 1, wherein FIG. 3 depicts the osmotic device operative embodiment for delivering a drug in the colon;

In the drawing figures and in the specification, like parts in related figures are illustrated by like numbers. The terms appearing earlier in the specification, and in the description of the drawing figures, as well as embodiments thereof, are further described elsewhere in this disclosure.

In the drawing figures and in the specification, like parts in related figures are identified by like numbers. The terms appearing earlier in the specification and in the description of the drawing figures, as well as embodiments thereof, are further detailed elsewhere in the disclosure.

DETAILED DESCRIPTION OF THE DRAWINGS

Figure 1:
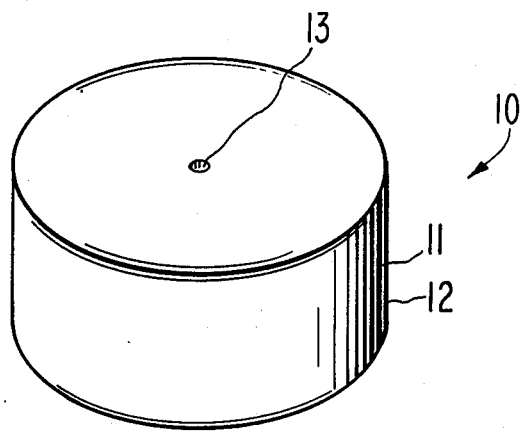
FIG. 1 is a view of an osmotic delivery device designed for orally administering a drug to the colonic region of the gastrointestinal tract.

Turning now to the drawing figures in detail, which drawings are examples of osmotic devices provided by the invention, and which examples are not to be construed as limiting, one example of an osmotic device is seen in FIG. 1 identified by the number 10. In FIG. 1, osmotic device 10 is sized, shaped and adapted for use as an orally administrable osmotic device. Osmotic device 10 comprises a body 11, a wall 12 and a passageway 13 in wall 12.

Figure 2:
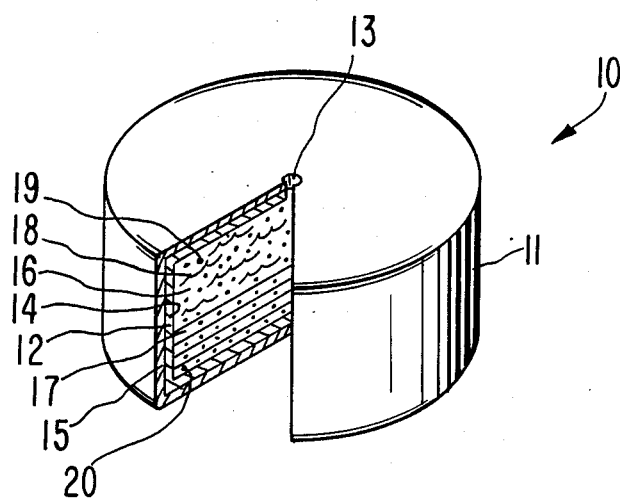

In FIG. 2, device 10 is seen in opened view for illustrating the structural members of osmotic, colonic delivery device 10. In FIG. 2, device 10 comprises body 11, wall 12 and at least one passageway 13 that extends through wall 12 and connects an internal compartments 14 with the exterior of device 10. Wall 12 comprises at least in part a semipermeable composition that is permeable to the passage of an external fluid present in the environment of use, such as aqueous and aqueous-like-fluids, such as biological fluids. Wall 12 is essentially impermeable to the passage of drug. Wall 12 is substantially inert, and it maintains its physical and its chemical integrity during the dispensing of a drug. Wall 12 comprises a composition that is non-toxic to animals including humans.

In FIG. 2, device 10 comprises means 15 for essentially delaying the delivery of a drug from device 10, during the passage of device 10 through the stomach. Means 15 comprises an exterior wall or coat on the exterior surface of wall 12. The exterior surface of wall 12 is the surface facing the environment of use, that is the gastrointestinal tract. Means 15 comprises a composition that maintains its physical and chemical integrity in an acidic environment such as the stomach. The phrase, "maintains its physical and chemical integrity," for the purpose of this invention, denotes that means 15 does not dissolve or disintegrate in an acidic environment. Means 14 is substantially impermeable to the passage of fluid and it prevents fluid from reaching the exterior surface of wall 12, thereby preventing passage of fluid through wall 12 into device 10. Means 12 consequently delays the release of drug from device 10 during means 14 tenure on the exterior surface of wall 12.

In FIG. 2, device 10 comprises wall 12 surrounding and defining an internal compartment 14. Internal compartment 14 comprises a first composition 16 and a second composition 17. First composition 16 comprises a beneficial drug 19 and a means 18 for delaying the delivery f drug 19 from device 10. Means 18 delays the delivery of drug 19 for a period of time approximately equal to the time required for device 10 to pass through the small intestine, usually about 2 to 4 hours. Means 18 comprises a rheological composition possessing resistance to flow in its initial substantially-dry state as device 10 enters the small intestine. Means 18 comprising the rheological composition begins to form a dispensable flowable composition as device 10 enter the small intestine and fluid from the small intestine enters device 10. Means 18 comprising the rheological composition, absorbs fluid over a 2 to 4 hour period thereby overcoming and changing its resistance to flow by forming a dispensable composition. Device 10 subsequently leaves the small intestine, enters the colon and delivers drug 19 in the colon.

Compartment 14 houses a second composition 17 that is in contacting relation with first composition 16. Second composition 17 is a driving force that expands and pushes dispensable first composition 16 from device 10. The second composition in operation imbibes fluid into a compartment 14, absorbs the imbibed fluid and expands in compartment 14. The continuous uptake of incoming fluid by composition 17 causes it to continuously expand and push composition 16 from device 10 into the colon. In one presently preferred embodiment second composition 17 comprises an osmopolymer, also known as a hydrophilic hydrogel, that exhibits an osmotic pressure gradient across a semipermeable wall 12 against an external fluid present in the gastro-intestinal tract. In another presently preferred embodiment, composition 17 comprises an osmopolymer and an osmagent 20. Osmagents are known also as osmotically effective compounds and they exhibit an osmotic pressure gradient across a semipermeable wall against a fluid present in the environment of use. The osmopolymer in cooperation with the osmagent both imbibe fluid into the second composition for optimizing the maximum expansion of composition 17 to an enlarged state for pushing dispensable composition 16 through drug releasing means 13 from device 10.

Figure 3:
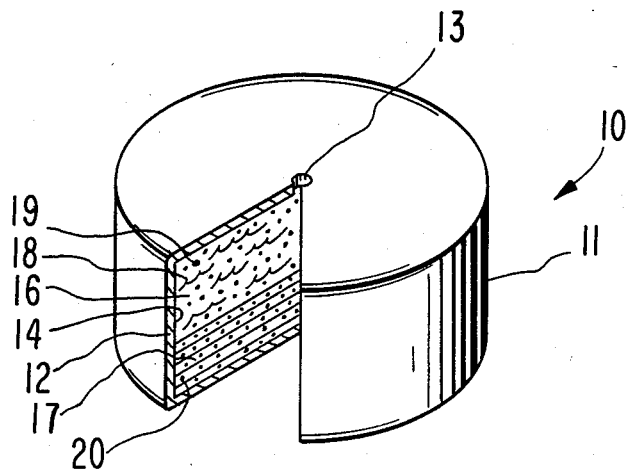

FIG. 3 is an opened view illustrating device 10 free of means 15 that substantially prevented passage of an exterior fluid into compartment 14. In FIG. 3, device 10 passes through the stomach and enters the small intestine substantially free of drug delivery in the small intestine while enroute to the colon.

Delivery system 10 as seen in FIGS. 1 through 3 can be made into many embodiments for oral use for releasing locally or systemically acting therapeutic drugs in the colon of the gastrointestinal tract. In one preferred embodiment the oral delivery system can have various conventional shapes and sizes such as round, eggshaped, kidney-bean shaped, and the like. These oral delivery systems can comprise a diameter of 5/16 inch to 9/16 inch, and the like. The oral dosage systems in another manufacture are sized and shaped as small tiny osmotic pills having a diameter of about 2 mm to 10 mm. The small dosage pills can be administered individually or as a plurality of small pills in a single piece or in a two piece capsule. The capsule can house 1, 5, or a plurality of small dosage pills from 1 to 100, and the like.

DETAILED DESCRIPTION OF THE INVENTION

In accordance with the practice of this invention, wall 12 comprises a composition that is permeable to the passage of fluid, substantially impermeable to the passage of drug, osmotic solutes, suspending agents, and the like. The composition does not adversely affect the beneficial drug, and the animal host. The selectively permeable materials comprising wall 12 are semipermeable materials that are insoluble in body fluids and they are non-erodible. Typical selective materials for forming wall 12 include semipermeable polymers known in the art as osmosis membranes. The polymeric compositions presently preferred for manufacturing wall 12 include a member selected from the group consising of cellulose acylate, cellulose diacylate, cellulose triacylate, cellulose ester, cellulose ether and cellulose ester-ether. Representative semipermeable polymers include cellulose acetate, cellulose diacetate, cellulose triacetate, dimethylcellulose acetate, cellulose acetate propionate, cellulose acetate butyrate, and the like. Semipermeable polymers are known in U.S. Pat. Nos. 3,173,876; 3,276,586; 3,541,005; 3,541,006; 3,546,142; 3,845,770; 3,916,899; 4,036,228; and 4,111,202.

Means 15 for delaying the passage of fluid through wall 12 comprises a composition that does not dissolve, disintegrate, or change its structural nature in the stomach, and during the period of time delivery device 10 passes through the stomach. Representative of compositions that keep their integrity in the acidic environment of the stomach comprise (a) a member selected from the group of phthalates consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinylacetate phthalate and the like; (b) a member selected from the group consisting of keratin, keratin sandaractolu, salol, salol beta-naphyl benzoate and acetotannin, salol with balsam of Peru, salol with tolu, salol with gum mastic, salol and stearic acid, and salol and shellac; (c) a member selected from the group consisting of formalized protein, formalized gelatin, and formalized cross-linked gelatin and exchange resins; (d) a member selected from the group consisting of myristic acid-hydrogenated castor oil-cholesterol, stearic acid-mutton tallow, stearic acid-balsam of tolu, and stearic acid-castor oil; (e) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (f) a member selected from the group consisting of abietic acid, methyl abietate, benzoin, balsam of tolu, sandarac, mastic with tolu, and mastic with acetyl alcohol; (g) a member selected from the group consisting of cellulose acetate phthalate with shellac, starch acetate phthalate, polyvinyl acid phthalate, 2-ethoxy-5-(2-hydroxyethoxy)-methylcellulose phthalic acid, acid phthalates of carbohydrates, zein, alkylresin unsaturated fatty acids-shellac, colophony, mixtures of zein and carboxymethylcellulose phthalate; (h) anionic polymers synthesized from methacrylic acid and methacrylic acid methyl ester, copolymeric acrylic resins of methacrylic acid and methacrylic acid methyl ester, copolymers of methacrylic acid and methacrylic acid methyl ester with dialkyl phthalates, copolymers of methacrylic acid and methacrylic acid methyl ester with dibutyl phthalate, and the like. The acid resistance materials are known in *Remington's Pharmaceutical Science*, (1965), 13th. Ed., pages 604–605, published by Mack Publishing Co., Eaton, Pa.; *Eudragit ® Coatings Rohm Pharma*, (1985); and U.S. Pat. No. 4,627,851.

The term, "drug 19," as used for the purpose of this invention embraces drugs that are administered in the colon to produce a therapeutic effect. The drugs include the drugs conventionally used in the treatment of colitis, ulcerative colitis, Crohn's disease, idiopathic prototis and other diseases of the colon. Representative drugs include salicylozosulfapyridine, also known as sulphasalazine, and salazopyrin; adrenocorticosteroids such as hydrocortisone, prednisolone, prednisolone phosphate, prednisolone sulfate, prednisone, prednisolone metasulpho-benzoate sodium, prednisolone sodium phosphate and the like; corticosteroids such as beclomethasone, beclomethasone acetate, beclomethasone valerate, beclomethasone propionate, beclomethasone dipropionate, and the like; cyclosporin; and the like. In another aspect, drug 19 also includes drugs for treatment of irritable bowel syndrome, or drug 19 alters bowel motility and fluid absorption, such drugs are represented by calcium channel blocking drugs, opiads, anticholinergics and benzodiazepides. The amount of drug in a delivery device 10 can be from 10 ng to 1.2 g, and the amount of drug in the tiny dosage forms is from 10 ng, to 20 mg, and the like.

Means 18 comprises drug 19 homogeneously distributed therein for delivering drug 19 to the colon. Means 18 is used for delaying the release of drug 19 for about 2 to 4 hours from delivery device 10 as delivery device 10 passes through the small intestine in a corresponding period of about 2 to 4 hours. Means 18 comprises a composition that is initially substantially dry as delivery device 10 enters the small intestine. In the presence of aqueous-biological fluid in the small intestine that passes into delivery device 10, the composition absorbs fluid, forms a thicken viscous composition, and continuously absorbs fluid to reduce its viscosity, thereby providing a dispensable composition. Compositions useful for this purpose comprise polymeric compositions having a molecular weight of about 200,000 to 350,000 and exhibit a viscosity at 25° C. of about 300 to 1800 centipoises of a 5% aqueous solution. One presently preferred composition comprises polyethers that hydrogen bond with water. Representative polymeric compositions include the polyethers, polyoxyethylene having a molecular weight of 250,000, polyoxyethylene having a molecular weight of 300,000, polyoxyethylene having a molecular weight of 350,000, and the like. Means 18 in another preferred embodiment comprises a hydroxypropylmethylcellulose having a molecular weight from 9,200 to 23,000 and a viscosity of 3 to 50 centipoises of a 2% aqueous solution at 20° C. as an aid for delaying drug release and in forming a dispensable composition.

Second composition 17 comprises means for interacting with aqueous and biological fluids, swelling or expanding for pushing the first composition from the delivery device. Second composition 17 comprises means for retaining a significant portion of imbibed and absorbed fluid within its molecular structure. Representative compositions comprise osmopolymers that are non-cross-linked or lightly cross-linked by covalent or ionic bonds. The osmopolymers can be of natural or of synthetic origin. The osmopolymers are hydrophilic polymers. Representative polymers for forming second composition 17 include poly(hydroxyalkylmethacrylate) having a molecular weight of from 30,000 to 5,000,000; poly(vinylpyrrolidone) having a molecular weight of from 10,000 to 360,000; anionic and cationic hydrogels; polyelectrolyte complexes; poly(vinyl alcohol) cross-linked with glyoxal, formaldehyde or glutaraldehyde and a degree of polymerization from 20,000 to 30,000; a mixture of cross-linked agar, methyl cellulose and carboxymethylcellulose; a water insoluble, water swellable copolymer reduced by forming a dispersion of finely divided copolymer of maleic anhydride with styrene, ethylene, propylene, butylene or isobutylene cross-linked with from 0.001 to about 0.5 moles of polyunsaturated cross-linking agent per mole of maleic anhydride in the copolymer; water swellable polymers of N-vinyl lactams; and the like.

In another presently preferred embodiment, second composition 17 comprises a member selected from the group consisting of acidic carboxy polymers having a molecular weight of 450,000 to 4,000,000; polyacrylamides; cross-linked water swellable indene-maleic anhydride polymers; polyacrylic acid having a molecular weight of 80,000 to 200,000; polyalkylene oxide polymers having a molecular weight of 100,000 to 8,000,000; starch graft copolymers; acrylate polymers; drister cross-linked polyglucan; and the like. Representative polymers that form hydrogels are known to the prior art in U. S. Pat. No. 3,865,108 issued to Hartop; U.S. Pat. No. 4,002,173 issued to Manning; U.S. Pat. No. 4,207,893 issued to Michaels, and in *Handbook of Common Polymers*, by Scott and Roff, published by Chemical Rubber Company, Cleveland, Ohio.

The osmotically effective compounds that can be used for the purpose of this invention comprise inorganic and organic compounds that exhibit an osmotic pressure gradient across semipermeable wall 12 against an external fluid. The osmotically effective compounds are also known as osmotically effective solutes and osmagents. The osmotically effective compounds in second composition 17 imbibe fluid into the second composition for increasing its expansion for urging the first composition from delivery device 10. Osmotically effective compounds used for the present purpose comprise magnesium sulfate, magnesium chloride, potassium sulfate, sodium sulfate, lithium sulfate, potassium acid phosphate, manitol, urea, magnesium succinate, tartaric acid, carbohydrates such as raffinose, sucrose, glucose, sodium chloride, and the like. The amount of osmotically effective compounds in the second composition generally will be from 0.01% to 40% or higher.

The expression, "exit means 13," as used herein, comprises means and methods suitable for the metered release of beneficial drug 19 from compartment 14 of dosage form 10. The exit means 13 include at least one passageway, orifice or the like, through wall 12 for communicating with compartment 14. The expression, "at least one passageway," includes aperture, orifice, bore, pore, porous element through which the drug can migrate, hollow fiber, capillary tube, porous overlay, porous insert, and the like. The expression also includes a material that erodes or is leached from wall 12 in the fluid environment of use to produce at least one passageway 13 in dosage form 10. Representative materials suitable for forming at least one passageway, or a multiplicity of passageways, include an erodible poly(glycolic) acid or erodible poly(lactic) acid member in the wall; a gelatinous filament; poly(vinyl alcohol); leachable materials such as fluid removable pore forming polysaccharides; salts, oxides, and the like. A passageway or a plurality of passageways can be formed by leaching a material such as sorbitol, lactose, or the like, from the wall. The passageway can have any shape such as round, triangular, square, elliptical, and the like, for assisting in the metered release of drug 19 from dosage form 10. Dosage form 10 can be constructed with one or more passageways in spaced apart relations, or more than one passageway on a single surface of dosage form 10. Passageways and equipment for forming passageways are disclosed in U.S. Pat. Nos. 3,845,770; 3,916,899; 4,063,064; and 4,088,864. Passageways for releasing a drug formed by leaching are disclosed in U.S. Pat. Nos. 4,200,098 and 4,285,987.

First composition 16 and second composition 17 are manufactured from well mixed individual composition forming members. For example a first composition is made as follows: first, each of the ingredients comprising a dosage form is independently screened and then blended together, except for a lubricant. Then, the homogeneous blend is wet granulated by adding a solvent such as anhydrous ethanol, and the wet ingredients mixed until a uniform blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a uniform blend. Then, the first composition is fed to a hopper of a compression machine, and the first composition pressed into the first layered composition. The process is repeated for the second composition. Typically about one-fourth to two tons of pressure are applied to yield the dosage form.

The dosage form can be made also by a dry granulation process of manufacture. The dry process comprises first mixing all the composition forming ingredients, except for the lubricant, passing the mixed ingredients through a grinding mill to a small mesh size, and then transferring the sized powder to a dry compactor. The compactor densifies the powder and is extruded as a sheet or ribbon which is then passed through a sizing mill to regrind the composition. The composition is ground to a small size, typically 20 mesh or smaller. Finally, a dry lubricant is added and the ingredients blended to produce the final composition. Then, the respective composition is fed to a bi-layer tablet press and each composition compressed into contacting layers comprising dosage form 10.

The wall of a dosage form, and the exterior delay coat can be formed by one technique using the air suspension procedure. This procedure consists in suspending and in tumbling the drug forming compartment in a current of air and a wall forming, or delay coat composition until, in either operating the wall or the delay coat is applied to the layered drug forming compartment. The air suspension procedure is well-suited for independently forming the wall on the delayed coat. The air suspension procedure is described in U.S. Pat. No. 2,799,241; in *J. Am. Pharm. Assoc.* Vol. 48, pp 451–59, (1959); and ibid., Vol. 49, pp 82–4, (1960). Dosage-forming devices can also be coated with the wall forming composition with a Wurster ® air suspension coater using methylene dichloride-methanol cosolvent 80/20 V/V, using 2.5 to 4% solids. The Aeromatic ® air suspension coater using a methylene dichloride/methanol cosolvent 87/13 v/v also can be used for applying the wall on the delayed coat. Other wall and delayed coating techniques such as pan coating can be used for proving the delivery device. In the pan coating system, wall forming, or delayed coating compositions are deposited by successive spraying of the compositions of the drug layer, push layer compartment forming cores, accompanied by tumbling in a rotating pan. A pan coater is used to produce a thicker wall or delayed coat. A larger volume of methanol can be used in a cosolvent to produce a thinner wall or delayed coat. Finally, the wall with the delayed coated compartment are dried in a forced air oven at 50° C. for a week to free the dosage form of solvent. Generally, the wall formed by these techniques will have a thickness of 2 to 20 mils with a presently preferred thickness of 4 to 10 mils. The delayed coat generally will have a thickness of 0.5 to 15 mils, usually 0.5 to 7.5 mils.

Exemplary solvents suitable for manufacturing the wall or the delayed coat include inorganic and organic solvents that do not adversely harm the wall, the delayed coat and the final delivery system. The solvents broadly include a member selected from the group consisting of alcohol, ketone, ester, ether, aliphatic hydrocarbons, halogenated solvents, cycloaliphatic solvents, aromatic, heterocyclic, aqueous solvents, and mixtures thereof.

The capsules used for housing a delivery device 10 comprises hard capsules and soft capsules. The hard capsule is composed of two parts, a cap and a body, which are fitted together after the body is filled with delivery device 10. This is done by slipping or telescoping the cap section over the body section, thereby completely surrounding and encapsulating delivery device 10. Hard capsules are made by dipping stainless steel molds into a bath containing a solution of a capsule forming material. Then, the molds are withdrawn, cooled and dried in a current of air. The capsule is stripped from the mold and trimmed to yield a member with an internal capsule lumen. The engaging cap that telescopically caps the capsule body is made in a similar manner. In another embodiment, the hard capsule can be made with each part having matched locking rings near the thin, opened end that permits joining and locking together the overlapping cap and body after filling with the delivery device. In this embodiment, a pair of matched locking rings are formed into the cap portion and the body portion, and these rings provide the locking means these rings provide the locking means for securely holding together the capsule. The capsules can be manually filled or they can be filled by machine.

The soft capsule used for the present invention, preferably in its final form, comprises one piece. Generally, the soft capsule is of scaled construction encapsulating the useful delivery device therein. The soft capsule is made by various processes including the plate process, the rotary die process, the reciprocating die process and the continuous process. Procedures for manufacturing capsules are known to the prior art in U.S. Pat. No. 4,627,850 issued to Deters, Theeuwes, Mullins and Eckenhoff; and in *Pharmaceutical Sciences* by Remington, Vol. XIV, pp 1671–77, (1970) published by Mack Publishing Co., Easton, Pa.

The following examples are merely illustrative of the present invention, and they should not be considered as limiting the scope of the invention in any way, as these examples and other equivalents thereof will become apparent to those versed in the drug delivery art in light of the present disclosure and the accompanying claims.

EXAMPLE 1

A delivery device for delivering a therapeutic drug to the colon of a human is made as follows: first, 22,642.85 grams of polyethylene oxide, having a molecular weight of about 300,000, and 1,250 grams of hydroxypropylmethylcellulose, having a molecular weight of 9,600, are dry screened through a Fitzmill ® comminuter using a 35 mesh stainless steel screen, and then transferred to a Hobart ® blender. Next, 107.15 grams of beclomethasone dipropionate is dissolved in anhydrous ethanol along with 1000 grams of polyvinylpyrrolidone. This granulating fluid is slowly added to the blender to produce a homogeneous blend. Next, the wet blend is passed through the comminuter using an 8 mesh stainless steel screen. The wet granules resulting from the screening process are dried in a forced air oven for about 18 hours at 30° C. Finally, the dry granules are passed through the comminuter using a 16 mesh stainless steel screen to yield the first composition comprising the drug beclomethasone dipropionate and the means for delaying its release from the device.

Next, the second composition is prepared as follows: 12,940 gram of polyethylene oxide, having a 5,000,000 molecular weight, 5,860 grams of sodium chloride, 1000 grams of hydroxypropylmethylcellulose, having a 11,300 molecular weight, and 200 grams of ferric oxide, are added to and passed through the comminuter using a 35 mesh stainless steel screen. The screened particles next are transferred to the blender and blend to produce a well mixed blend, and to the blending ingredients anhydrous ethanol is added as a granulating fluid. Next, the wet blend is transferred to the commuter using a 7 mesh stainless steel screen. Then, the wet granules are transferred to drying sheets and dried in a forced air oven at 30° C. for about 18 hours. The dried granules are passed through the comminuter using a 16 mesh stainless steel screen to yield the second composition comprising means for pushing the first composition from the delivery device.

Next, he first composition and the second composition are pressed into a first layer and into a second layer in a tableting machine using a 3/16 inch punch and die. The first composition weighed 23 mg and it comprises 0.1000 mg of beclomethasone dipropionate, 1.1666 mg of hydroxypropylmethylcelluose, 21.1321 mg of the polyethylene oxide, and 0.9333 mg of the polyvinylpyrrolidone; the second composition comprises 10.784 mg of the polyethylene oxide coagulant, 4.8837 mg of sodium chloride, 0.8384 mg of hydroxypropylmethylcellulose and 0.1667 mg of ferric oxide.

Next, a semipermeable wall is applied around the comprised contacting laminated compositions. The wall forming composition comprises 97 wt % of cellulose acetate having an acetyl content of 43.5%, and 3 wt % of polyethylene glycol 3350. The wall forming ingredients are dissolved in a cosolvent comprising 80:20 wt/wt methylene chloride-methanol comprising 5% solids. The wall is formed in an Accela-Cota® pan coater to an approximate thickness of 3 mils (0.076 mm) to provide a coating weight of 5 mg. After drying, and removing the cosolvent, a 0.25 mil orifice is laser drilled in the semipermeable wall to the first composition.

Next, an outside wall, comprising means for delaying the release of drug from the device during the devices' passage through an acidic environment, is coated onto the outside surface of the semipermeable wall. The outside wall forming composition comprises 85 wt % of a copolymer of (methacrylic acid and methacrylic acid methyl ester, also known as Eudragit® S-100) and 15 wt % of acetyltriethylcitrate, in 95% ethanol to provide 3% solids. The outside wall is applied in a 24 inch Accela-Cota® pan coater to apply a 3 mil (0.076 mm) wall.

The delivery devices made by the above procedure are dried in a humidity oven for 48 hrs at 50% relative humidity. Then, the delivery devices are dried an additional 24 hrs at 50° C. in a forced air oven.

Figure 4:
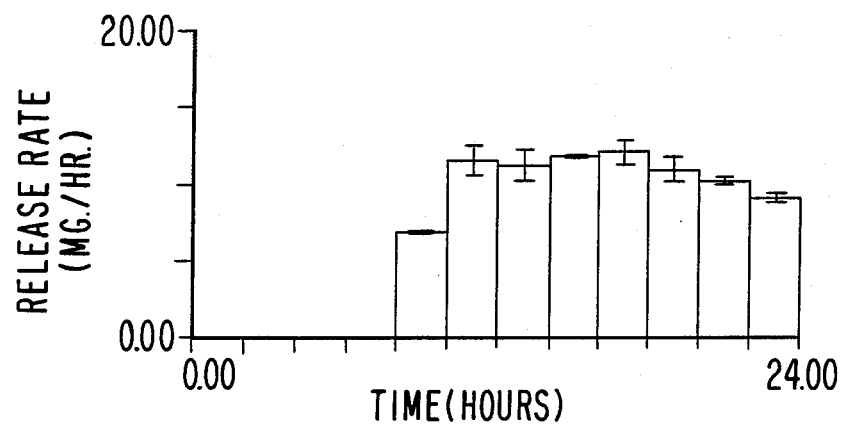
FIGS. 4 and 5 are graphs depicting the release rate pattern and the cumulative amount of drug released over time for a delivery device provided by the invention.
Figure 5:
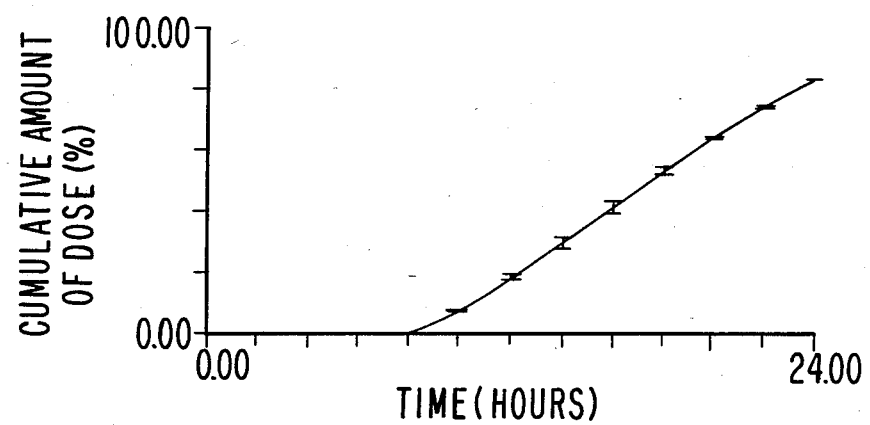
Figure 6:
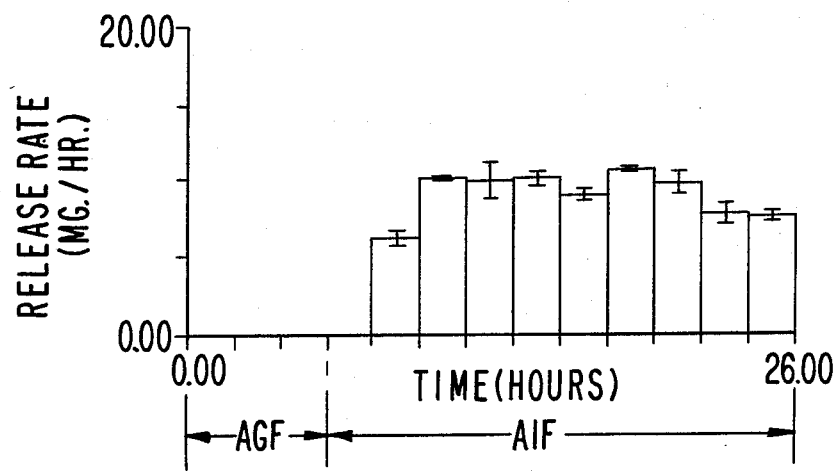
FIGS. 6 and 7 are graphs depicting the in vitro release rate performance of a device in acid and base media, both per unit time, and the cumulative amount released over time.
Figure 7:
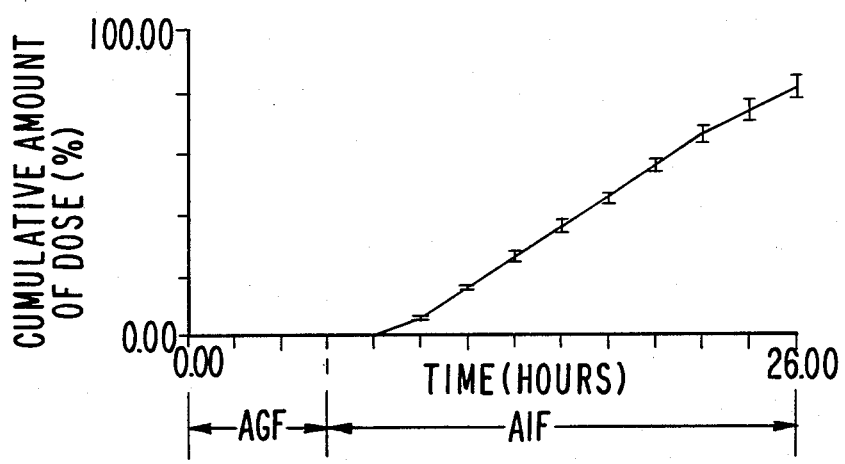
Figure 8:
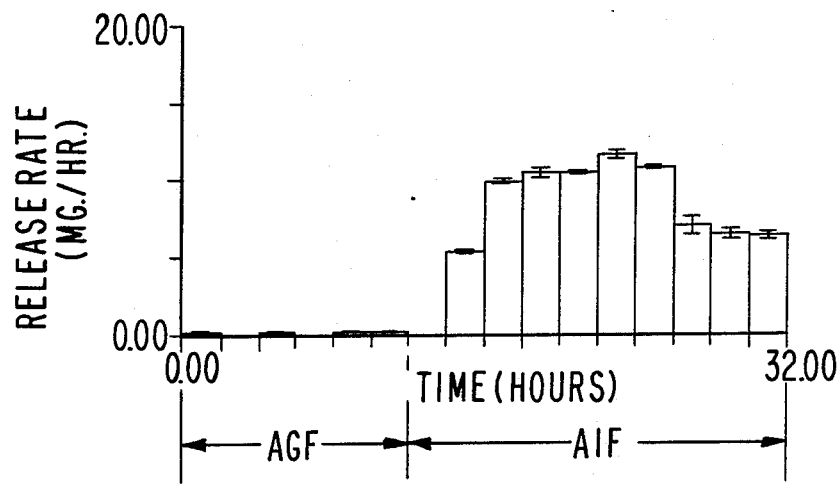
FIGS. 8 and 9 are graphs depicting the release rate patterns wherein the release rate is measured over a longer period of time in artificial gastric and artificial intestinal juice; and, FIG. 10 is a graph indicating the viscosities as a function of water dilution and at low shear rate for polymers used for providing the devices of this invention.
Figure 9:
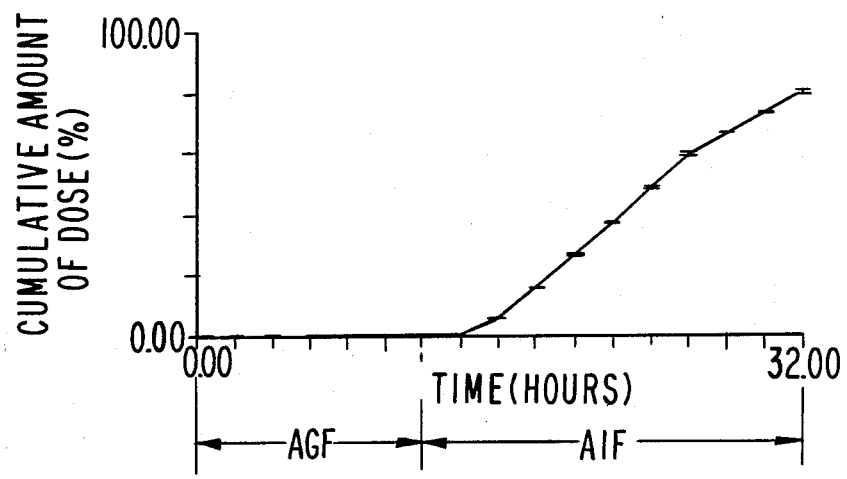

Accompanying FIG. 4 illustrates the release rate in mg/hr from the delivery device measured in four hours of artificial gastric fluid then in artificial intestinal fluid. FIG. 5 depicts the cumulative amount of drug release in artificial gastric fluid than in artificial intestinal fluid. The bars represent minimum and maximum average measurements. FIG. 6 and FIG. 7 depict the release rate per unit time and the cumulative amount released measured in artificial gastric fluid, seen as AGF in the figures, and in artificial intestinal fluid, seen as AIF in the figures, over a longer period of time for the same dispensing device. In FIG. 6 and FIG. 7, the dispensing device is in the artificial gastric fluid six hours, then placed in artificial intestinal fluid. In the intestinal fluid the device exhibited a two hour start-up for delivering the drug. FIG. 8 and FIG. 9 illustrate the release rate in micrograms per hour and the cumulative amount released for the same device wherein the delivery patterns are ascertained over a thirty-two hour period of time. In FIGS. 8 and 9 the device is in artificial gastric fluid twelve hours then in the artificial intestinal fluid. The device releases after a delay of about three hours in the artificial intestinal fluid. Artificial gastric and intestinal fluid are known to the art in *The United States Pharmacopoeia*, Twentieth Revision, p 1105, published 1980. Accompanying FIG. 9 depicts the cumulative amount of drug release in the artificial intestinal fluid. The bars represent minimum and maximum average measurements.

In a presently preferred embodiment, 5 delivery devices are encapsulated in a number 2 gelatin capsule. Each delivery device contains 0.100 mg (100 μg) of beclomethasone dipropionate and total delivery system delivers 500 μg of beclomethasone dipropionate to the colon.

EXAMPLE 2

The procedure described in Example 1 is followed with all conditions as set forth, except that in these examples the drug steroid is a member selected from the group consisting of beclomethasone, beclomethasone 17-propionate, beclomethasone 21-acetate, beclomethasone butyrate, and beclomethasone dipropionate monohydrate.

EXAMPLE 3

Delivery device are made comprising salicylazosulphayridine for treating Crohn's disease, and with an outer wall comprising a member selected from the group consisting of cellulose acetyl phthalate, cellulose diacetyl phthalate, cellulose triacetyl phthalate, cellulose acetate phthalate, hydroxypropylmethylcellulose phthalate, sodium cellulose acetate phthalate, cellulose ether phthalate, cellulose ester phthalate, and methylcellulose phthalate.

EXAMPLE 4

Delivery devices for delivering a drug to the colon are made according to the present examples wherein the drug is a member selected from the group consisting of hydrocortisone, prednisolone, prednisolone phosphate and prednisone, and wherein the wall for delaying drug release in an acidic environment is a member selected from the group consisting of polymers of methacrylic acid and methacrylic acid methyl esters, a copolymer of methacrylic acid and methacrylic acid methyl ester with dialkyl phthalates, and a copolymer of methacrylic acid and methacrylic methylester with dibutyl phthalate.

EXAMPLE 5

A series of hydrophilic polymers were studied for ascertaining viscosity at low shear properties useful for manufacturing means 18 for delaying release of drug in the small intestine.

Figure 10:
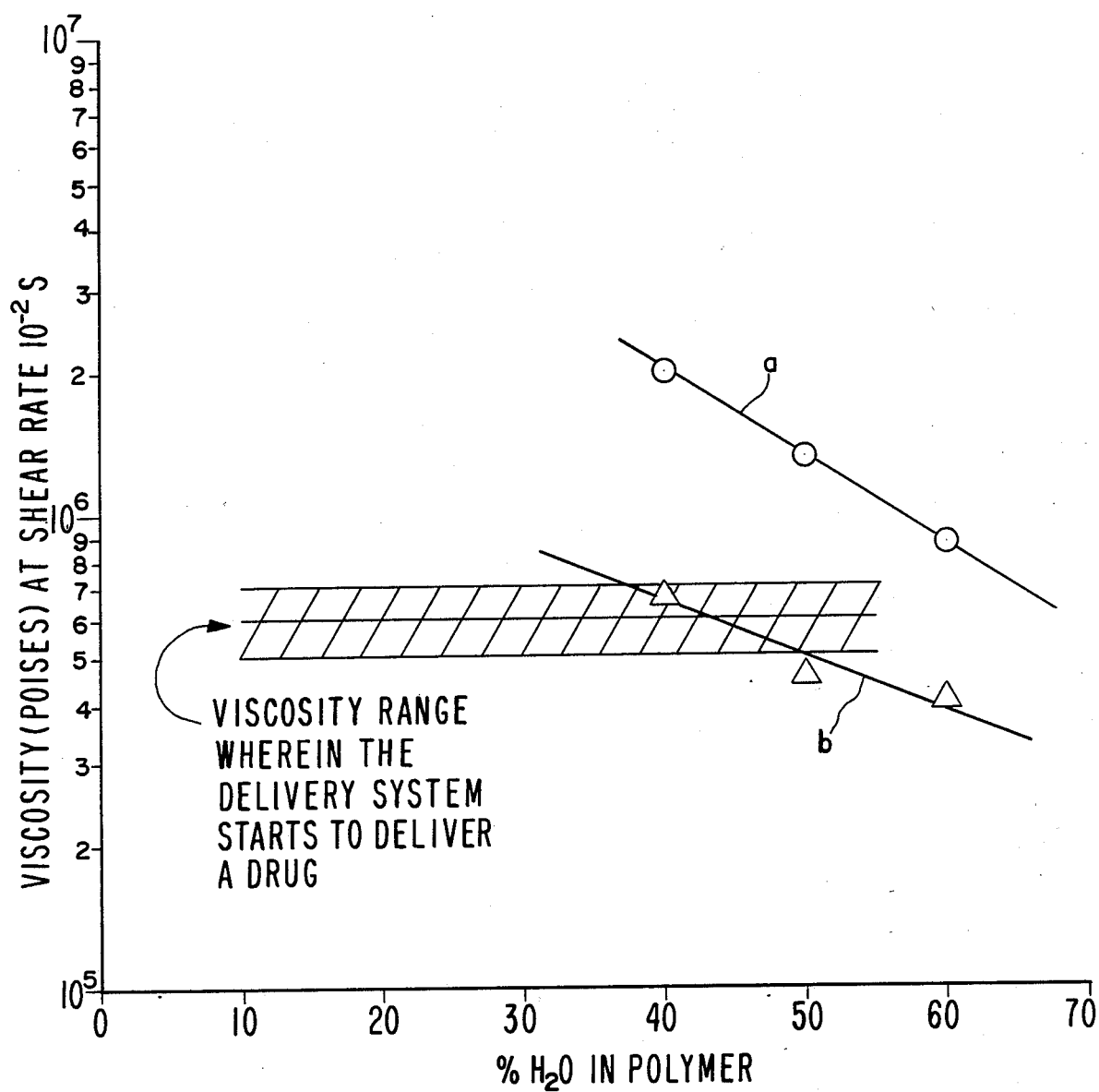

Accompanying FIG. 10 indicates the flow properties expressed as viscosities of a number of hydrophilic polymers. In FIG. 10, the line identified by the letter "a" indicates the polymer polyethylene oxide having a molecular weight of about 300,000, the line identified by the letter "b" denotes polyethylene oxide having a molecular weight of about 200,000. The viscosity studies were done at different concentrations of aqueous solutions at 37° C. using the Rheometer®, RM5-800, manufactured by Rheometric Inc., Piscataway, N.J. The stud denotes, as seen in FIG. 10, that for a hydrophilic polymer having a viscosity of approximately $5-7\times10^5$ poises, at a shear rate of $10^{-2}$ seconds, the hydrophilic polymer begins to enter a dispersable phase with 40% of water. Thus, for a polymer having a molecular weight of about 300,000 the polymer, to enter a dispersible phase, must absorb water for at least two hours or longer to reach a $5-7\times10^5$ poises at a water content of 60–70%.

EXAMPLE 6

The procedure of Example 1 is followed with the manufacturing procedures as previously set forth, except that the outside wall forming composition comprises 85 wt % of a copolymer of trimethyl ammonium ethylmethacrylate chloride-methylmethacrylate-ethylacrylate in the ratio of 5:65:30, and 15 wt % acetyltriethylcitrate, in 95% ethanol, to provide 3% solids, and the drug is 5-aminosalicylic acid.

EXAMPLE 7

A presently preferred embodiment of the invention pertains to a method for delivering a drug to the colon of a human at a controlled rate and continuously, which method compriese the steps of: (A) admitting orally into the human's gastrointestinal tract a dispensing device comprising: (1) a wall comprising an inside surface that surrounds and forms an internal compartment, said wall comprising a composition permeable to the passage of a biological fluid; (2) means on the outside surface of the wall for delaying fluid access to the wall and, consequently, delaying the passage of fluid through the wall during the period of time the dispensing device passes through the stomach; (3) a drug in the compartment for delivering drug to the colon; (4) means in the compartment for delaying the delivery of drug from the device during the period of time the device is in the small intestine; (5) means in the compartment for pushing the drug and the means for delaying its release from the device; (6) exit means in the device for delivering the drug from the device; (B) imbibing fluid through the wall into the compartment for converting the means for delaying the delivery of drug to a dispensable formulation; (C) imbibing fluid into the compartment at a rate determined by the permeability of the wall and the osmotic pressure gradient across the wall, thereby causing the means for pushing to expand and push the drug and dispensable formulation from the deivce; and (D) delivering the beneficial drug formaultion from the compartment by the expandable means continuously expanding thereby causing the drug to be dispensed through the exit means at a therapeutically effective amount at a controlled rate over a period of time to the colon of a human.

EXAMPLE 8

The procedure of Examples 1 and 8 are repeated with all conditions as set foth, except that the copolymer (methacrylic acid and methacrylic acid methyl ester S-100) is replaced by the copolymer of (methacrylic acid and methacrylic acid methyl ester L-100).

Inasmuch as the foregoing specification comprises preferred embodiments of the invention it is understood that variations and modifications may be made herein, in accordance with the inventive principles disclosed, without departing from the scope of the invention.

We claim:

1. A device for delivering a drug to the colon of an animal environment of use, the device comprising:
   (a) a wall comprising at least in part a composition permeable to the passage of fluid present in the environment of use and substantially impermeable to the passage of drug, which wall surrounds;
   (b) a compartment;
   (c) means in contact with the surface of the wall that faces the environment of use for substantially delaying the delivery of drug when the device is in the stomach;
   (d) a drug for delivering to the colon in the compartment;
   (e) first means in the compartment for substantially delaying the delivery of drug when the device is in the intestine;
   (f) second means in the compartment in contact with the first means for pushing the first means from the compartment; and,
   (g) exit means in the wall communicating with the compartment and the exterior of the device for delivering the drug to the colon.

2. A device for delivering beclomethasone to the colon of the gastrointestinal tract, the device comprising:
   (a) a wall that surrounds and defines a compartment and comprises at least in part a composition permeable to the passage of fluid;
   (b) means in contact with the wall for substantially preventing the delivery of beclomethasone while the device passes through the stomach of the gastrointestinal tract;
   (c) a therapeutic amount of beclomethasone in the compartment;
   (d) means in the compartment for substantially delaying the delivery of beclomethasone while the device passes through the small intestine;
   (e) means in the compartment for pushing beclomethasone from the device to the colon; and,
   (f) exit means in the wall communicating with the compartment for delivering beclomethasone to the colon.

3. The device for delivering beclomethasone according to claim 2, wherein the beclomethasone is a monoester.

4. The device for delivering beclomethasone according to claim 2, wherein the beclomethasone is a diester.

5. The device for delivering beclomethasone according to claim 2, wherein the beclomethasone is present in the compartment as a member selected from the group consisting of acetate, butyrate, valerate, propionate, dipropionate and divalereanate.

6. The device for delivering beclomethasone according to claim 2, wherein the device is in a capsule.

7. The device for delivering beclomethasone according to claim 2, wherein from 3 to 6 of said devices are present in a capsule.

8. A device for delivering a therapeutic steroid to the colon of a warm-blooded animal, wherein the device comprises:
   (a) a wall that surrounds and forms a compartment, which wall comprises at least in part a composition permeable to the passage of fluid;
   (b) means in contact with the wall for substantially delaying delivery of the steroid while the device is in the stomach;
   (c) a compartment;
   (d) a dose amount of a therapeutic steroid in the compartment;
   (e) means in the compartment for substantially delaying the delivery of the steroid from the compartment while the device is in the small intestine;
   (f) means in the compartment for pushing the steroid from the compartment; and,
   (g) means in the wall connecting the compartment with the exterior of the device for delivering the steroid from the device over time to the colon.

9. The device for delivering a therapeutic steroid to the colon of a warm blooded animal according to claim 8, wherein the steroid is a member selected from the group consisting of an adrenocorticosteroid and a corticosteroid.

10. The device for delivering a therapeutic steroid to the colon of a warm-blooded animal according to claim 8, wherein the steroid is a member selected from the group consisting of hydrocortisone, prednoisolone, prednisolone phosphate, prednisone, prednisolone metasulphobenzoate, and prednisolone sodium phosphate.

11. A device for delivering salicylazosulfapyridine to the colon of a human, wherein the device comprises:

(a) a wall comprising at least in part a composition permeable to the passage of fluid, which wall surrounds and forms;
(b) a compartment;
(c) means in contact with the wall for substantially delaying the delivery of salicylazosulfapyridine while the device is in the stomach;
(d) a dose amount of salicylazosulfapyridine in the compartment;
(e) means in the compartment for substantially delaying the release of salicylazosulfapyridine from the device while the device is in the small intestine;
(f) means in the compartment for pushing salicylazosulfapyridine from the device; and,
(g) means in the wall connecting the compartment with the exterior of the device for delivering the salicylazosulfapyridine from the device to the colon of the human.

12. The device for delivering salicylazosulphapyridine according to claim 11, wherein the wall comprises an exterior surface and the means for delaying passage of fluid through the wall is on the exterior surface.

13. A method for administering beclomethasone to the colon of the gastrointestinal tract of a human, which method comprises:
(a) admitting an osmotic device orally into the human, said osmotic device comprising:
(1) a wall comprising at least in part a composition permeable to the passage of an exterior fluid and substantially impermeable to the passage of beclomethasone, the wall surrounding and forming;
(2) a compartment;
(3) means in contact with the wall for substantially delaying the delivery of beclomethasone while the device passes through the stomach;
(4) a dosage amount of beclomethasone in the compartment;
(5) means in the compartment for substantially delaying the delivery of beclomethasone from the device while the device passes through the small intestine;
(6) means in the compartment for pushing beclomethasone from the device;
(7) means in the wall for releasing beclomethasone from the device; and,
(b) administering the beclomethasone to the colon by the device passing into the colon wherein the device administers the beclomethasone over time.

14. The method for administering beclomethasone to the colon of the gastrointestinal tract of a human according to claim 13, wherein the beclomethasone is a dipropionate.

15. The method for administering beclomethasone to the colon of the gastrointestinal tract of a human according to claim 13, wherein the beclomethasone comprises a member selected from the group consisting of a monoester and a diester.

16. A method for administering a drug to the colon of the gastrointestinal tract of a warm-blooded animal, which method comprises:
(a) admitting an osmotic device orally into the gastrointestinal-tract of the warm-blooded animal, said device comprising:
(1) a wall comprising an outside and an inside surface, which wall comprises at least in part a composition permeable to the passage of fluid, and substantially impermeable to the passage of drug, the wall surrounding and forming;
(2) a compartment;
(3) means in contact with the outside of the wall for substantially delaying the delivery of drug from the device during the time the device is in the stomach;
(4) a dosage amount of a colon administrable drug in the compartment;
(5) means in the compartment for substantially delaying the delivery of drug during the time the device is in the small intestine;
(6) means in the compartment for pushing the drug from the compartment;
(7) means in the wall for releasing the drug from the compartment; and,
(b) administering the drug to the colon by the device entering the colon wherein the drug is administered over time.

17. The method for administering the drug to the colon of the gastrointestinal tract according to claim 16, wherein the drug is administered for treating Crohn's disease.

18. The method for administering the drug to the colon of the gastrointestinal tract according to claim 16, wherein the drug is administered for treating colitis.

19. The method for administering the drug to the colon of the gastrointestinal tract according to claim 16, wherein the drug is sulphasalazine.

20. The method for administering the drug to the colon of the gastrointestinal tract according to claim 16, wherein the drug is cyclosporin.

21. The method for administering the drug to the colon of the gastrointestinal tract according to claim 16, wherein more than one device is administered in a capsule.

22. The method for administering the drug to the colon of the gastrointestinal tract according to claim 16, wherein the drug is 5-aminosalicylic acid.

* * * * *